United States Patent
Vanaja et al.

(10) Patent No.: US 8,357,275 B2
(45) Date of Patent: Jan. 22, 2013

(54) POTENTIOMETRIC CHOLESTEROL SENSOR FOR THE QUANTITATIVE ESTIMATION OF TOTAL CHOLESTEROL IN HUMAN BLOOD SERUM

(75) Inventors: Sunkam Vanaja, Hyderabad (IN); Mandapati Jayalakshmi, Hyderabad (IN); Sunkara Sakunthala Madhavendra, Hyderabad (IN); Mandapati Mohan Rao, Hyderabad (IN); Mannepalli Lakshmi Kantam, Hyderabad (IN); Isukapally Margaret, Hyderabad (IN); Vinod Kumar Khanna, Pilani (IN); Shamim Ahmad, New Delhi (IN); Yogendra Kumar Jain, Jaipur (IN); Chandra Sekhar, Pilani (IN)

(73) Assignee: Council of Scientific & Industrial Research, New Delhi (IN)

( * ) Notice: Subject to any disclaimer, the term of this patent is extended or adjusted under 35 U.S.C. 154(b) by 512 days.

(21) Appl. No.: 12/528,758

(22) PCT Filed: Feb. 20, 2008

(86) PCT No.: PCT/IN2008/000100
§ 371 (c)(1),
(2), (4) Date: Aug. 26, 2009

(87) PCT Pub. No.: WO2008/104992
PCT Pub. Date: Sep. 4, 2008

(65) Prior Publication Data
US 2010/0147683 A1    Jun. 17, 2010

(30) Foreign Application Priority Data
Feb. 26, 2007 (IN) .............................. 394/DEL/2007

(51) Int. Cl.
*G01N 27/26* (2006.01)
*G01N 33/92* (2006.01)
*G01N 33/543* (2006.01)
*H01L 21/30* (2006.01)

(52) U.S. Cl. .................. 204/403.01; 257/253; 438/197; 438/49; 435/11; 435/7.1; 436/531; 436/71; 525/50

(58) Field of Classification Search ............. 204/403.01; 257/253; 435/11, 7.1; 438/197, 49; 436/531, 436/71; 525/50
See application file for complete search history.

(56) References Cited

U.S. PATENT DOCUMENTS
2002/0006632 A1* 1/2002 Ponnampalam et al. .... 435/7.92

FOREIGN PATENT DOCUMENTS
WO    WO 2005/075995    *    8/2005

OTHER PUBLICATIONS

Physics of Semiconductor Devices, Sze et al., 2007, pp. 765-771.*
Thermo Scientific (Product Information page for 3-Aminopropyltriethoxysilane downloaded Jun. 18, 2012).*
Piletsky et al. (Sensor Actuators B 1999; 60, pp. 216-220).*
Whitcombe et al. (J.Am.Chem.Soc. 1995, 117, 7105-7111).*

* cited by examiner

Primary Examiner — Jeffrey T Barton
Assistant Examiner — Jennifer Dieterle
(74) Attorney, Agent, or Firm — K&L Gates LLP (57) ABSTRACT

The present invention provides a novel sensor for the estimation of total cholesterol in human blood serum using molecular imprint of cholesterol. Human blood serum contains 150-250 mg/dl cholesterol. The present invention provides a sensor device and a process for the fabrication of ISFET (Ion Selective Field Effect Transister) coated with molecular imprint of cholesterol on the $SiO_2+Si_3N_4$ dielectric gate of the said electrode. The molecular imprint of cholesterol (MIPC) anchored in to a silica matrix sensing material is identified as a sensing material which has specific selectivity towards the cholesterol in presence of other organic constituents in human blood serum.

13 Claims, 7 Drawing Sheets

The schematic cross-section of cholesterol ISFET.

Fig. 1

Fig. 2. The schematic cross-section of cholesterol ISFET.

1: P-substrate
2, 3: N$^+$ source and drain regions
4, 5: Terminal connections for source and drain
6: Substrate connection which is grounded
7: Field oxide
8: SiO$_2$+Si$_3$N$_4$ gate dielectric
9: MIPC layer

Fig. 7

POTENTIOMETRIC CHOLESTEROL SENSOR FOR THE QUANTITATIVE ESTIMATION OF TOTAL CHOLESTEROL IN HUMAN BLOOD SERUM

FIELD OF INVENTION

The present invention relates to a novel potentiometric sensor for the quantitative estimation of total cholesterol in human blood serum. Particularly, the present invention relates to a novel potentiometric sensor for the quantitative estimation of total cholesterol in human blood serum using molecular imprint of cholesterol (MIPC) as sensing material. More particularly, the present invention relates to a novel potentiometric sensor wherein a coating of MIPC was applied on the gate of ISFET which senses the cholesterol present in the human serum.

BACKGROUND OF THE INVENTION

Total Cholesterol monitoring in human blood serum is one of the most important routine analysis performed in the clinical laboratory. Heart disease is the number one cause of death in the world. Epidemiological studies have shown a strong correlation between coronary heart disease and blood cholesterol levels. The determination of cholesterol is very important in clinical diagnosis since a high serum cholesterol level is mainly related to arteriosclerosis and myocardial infarction. Arteriosclerosis results due to the deposition of fatty acids on the inner walls of arteries i.e., the smooth muscle cells of tunica media which proliferate and migrate to involve the tunica intima and produce the plaque. This does not happen in a single day but throughout the life time depending on the life style of human beings. There are small depositions of lipid in arterial walls even in the first decade of life and they are known as 'fatty streaks'. They may have no pathological significance except as an indication of the ability of the arterial wall to accumulate lipid. In the third decade of life, probably in the most individuals in industrialized societies, the amount of lipid, especially cholesterol ester accumulates leading to the development of atheroma. This primary lesion causes damage to the endothelial cells that line the intima. The damage may be caused by various factors including hypertension, cigarette smoking, viral attack and high lipid concentration. Further damage of the arteries results in permeability of the endothelial lining permitting blood platelets to enter the tunica media which produces the following two effects: (1) blood platelets aggregation and release of mitogenic agents that cause the smooth muscle cells to proliferate; (2) smooth muscle becomes exposed to much higher concentrations of the LDL (Lower density Lipoprotein) than the normal expected one probably by a non-specific endocytotic uptake process. The LDL enters the smooth muscle cells and is degraded by the enzymes of the lysosomes. Most of the amino acids and fatty acids leave the cell but cholesterol remains and becomes esterified to form cholesterol ester overloading the cell. As the proliferating cells migrate to the tunica intima, they synthesize collagen, glycosaminoglycans and elastin that may help to strengthen the arterial wall at the site of the original damage, thus initiating the plaque formation. The incidence of coronary heart disease shows a positive correlation with plasma cholesterol concentration and the dietary intake of saturated fat.

The myocardium (inner wall of the heart) is supplied with blood through the coronary arteries. A severe reduction in diameter due to atherosclerosis together with the occurrence of one or more blood clots within the artery or arteriole can produce complete occlusion. This results in failure of blood supply to part of the myocardium which in turn leads to the failure of the normal contractile activity in that part of the myocardium. If the artery which is occluded is large, the proportion of the myocardium without any blood supply is likely to be large. When a tissue is normally supplied with blood and the blood supply is removed, the tissue is said to be ischaemic. Irreversible damage results after about 20 minutes of ischaemia. Such damage means that portion of the myocardium dies and will eventually be replaced by fibrous tissue provided that the patient survives the initial trauma due to the occlusion. This is known as myocardial infarction.

Figure 1:
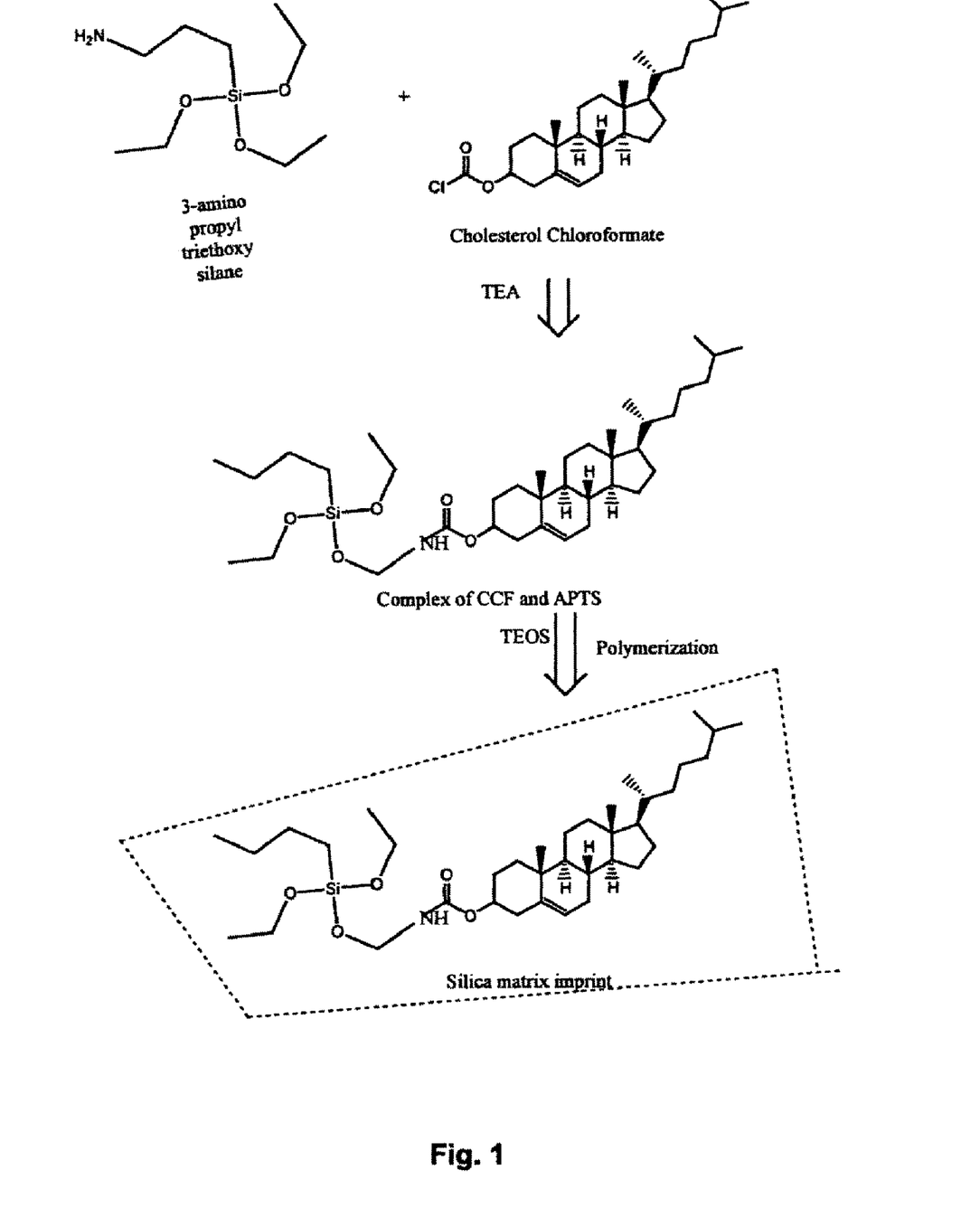
FIG. 1. Schematic representation of the preparation of molecular imprint of cholesterol.

Plasma/whole or total cholesterol constitutes different lipoprotein fractions (Low density lipoproteins (LDL). Very low density lipoproteins (VLDL) and High density lipoproteins (HDL). LDL is the major contributor to total plasma cholesterol in humans, accounting for one-half to two-thirds of the plasma cholesterol. The chemical composition of LDL lipoproteins is 55% free cholesterol and cholesterol esters, 5% triglycerides, 20% phospholipids and 20% proteins; the proteins are apolipoproteins B-100. The structure of cholesterol is ($C_{27}H_{46}O$) and is a yellowish crystalline solid (FIG. 1). Due to the presence of OH group, cholesterol is weakly amphiphilic. Cholesterol is insoluble in water and soluble in organic solvents such as choloroform, benzene, ether etc. The cholesterol cannot be degraded to $CO_2$ and $H_2O$. Cholesterol (50%) is converted to bile acids, excreted in faeces, serves as a precursor for the synthesis of steroid hormones, vitamin D, coprostanol and cholesterol. In adults the normal LDL-cholesterol is about 70-200 mg/dl while HDL-cholesterol is around 30-60 mg/dl. Increase in plasma HDL cholesterol is beneficial to the body, since it protects the body from atherosclerosis and coronary heart diseases (CHD). On the other hand increase in LDL—cholesterol is harmful to the body as it may lead to various complications, including CHD. Increase in plasma cholesterol (>250 mg/dl) concentration is known as hypercholesterolemia and is observed in many disorders like Diabetes mellitus, Hypothyroidism, obstructive jaundice and Nephrotic syndrome. Hypercholesterolemia is associated with atherosclerosis and coronary heart diseases (CHD). A decrease in the plasma cholesterol, although less common, is also observed along with the disorders hyperthyroidism, pernicious anemia, malabsorption syndrome, hemolytic jaundice etc.

A number of cholesterol biosensors have been developed over the past 30 years. Fibre-optic fluorescence, Fibre-optic luminescence, Potentiometric, Spectrophotometric, Amperometric and Fluorometric biosensors, which determine cholesterol enzymatically. Some of these methods suffer from interference from other substances found in the serum such as ascorbic acid and uric acid. Amperometric and potentiometric methods have been researched to determine cholesterol. The major disadvantages of these types of transducers include the need for calibration of the sensor both before and after the measurement, the lifetime of the sensor is short, and the oxidation of other electrochemically active species (known as interferents) present in the test sample may lead to false positive signals. The major interferents are ascorbic and uric acid. The use of polymer layers, which are more selective for the analyte of interest to eliminate or reduce the interferences.

Potentiometry using ion selective electrodes (ISE) is the method of choice due to the easy and fast performance of the assay. About 200 million clinical assays are performed using ISEs in the USA. It is well-known that ion selective electrodes are based on the use of a water-insoluble membrane that can be considered as a water-immiscible liquid of high viscosity, containing an ionophore which binds selectively the ion of interest and it generates a membrane potential. Potentiometric detection based on ion-selective electrodes, as a simple method, offers several advantages such as speed and ease of preparation and procedures, simple instrumentation, relatively fast response, wide dynamic range, reasonable selectivity and low cost. Besides, they are ideally suitable for on-site analysis and, nowadays, were found to be applicable in the analysis of some biologically relevant ions, process control and environmental analysis. Miniaturization of the system is realized using silicon technology. The cholesterol concentration is measured potentiometrically using ISFET coated with molecular imprint of cholesterol in combination with an Ag/AgCl reference electrode integrated on the same chip. To overcome problems resulting from a long time contact of the sensor with protein-containing sample solution, an automated measuring protocol was applied where the sensor is brought in contact with the sample only for short time segments. The frequency of sample/conditioning solution cycles depend on the diagnostic demand. In this way the active sensing area of the sensor is cleaned time to time. Furthermore, the sensor signal in the cleaning solution serves as a calibration point.

Molecular imprinting is a newly developed methodology that provides versatile receptors efficiently and economically. Molecular-imprinting polymerization (MIP) is a technique for creating recognition sites for an analyte molecule in a synthetic polymeric substrate. These artificially-generated recognition sites have their shapes, sizes and functionalities complementary to the analyte, and are capable of rebinding the analyte molecules in preference to other closely related structures. It aims to create solid materials. All we need are functional monomers, templates, solvents, and cross linking agents. Polymerization is followed by the removal of the template. During these procedures, a snapshot of the system is taken so that the resulting molecular assembly exclusively binds this template as well as its analogues. The uses of imprinted polymers in several analytical techniques, including liquid chromatography, capillary electrophoresis, capillary electrochromatography, solid phase extraction, and immunoassay have been investigated. These studies have included printing of several types of drug compounds and related substances, such as antibiotics of various types, beta-blocking agents, benzodiazepines, immunosuppressants, local anesthetics, opiates, steroids and xanthines, as well as triazine type herbicides. An advantage inherent to molecular imprinting, which has repeatedly been testified by the many examples above, is the possibility to synthesize sorbents with selectivity pre-determined for a particular analyte. The key step of the technique is the polymerisation of functional and cross-linking monomers in the presence of a templating ligand, or imprint species. Subsequent removal of the imprint molecules leaves behind 'memory sites', or imprints, in the solid, highly cross-linked polymer network. It is believed that the functional monomers become spatially fixed in the polymer via their interaction with the imprint species during the polymerization reaction. The result is the formation of imprints, which are complementary, both sterically and chemically, to the templating ligand in the polymer. These imprints enable the polymer to rebind selectively the imprint molecule from a mixture of the closely related compounds.

In general, molecular imprinting involves the following three steps. (1) Complex formation of a given target molecule (template molecules) with polymerizable monomers bearing functional group(s) capable of interacting with the target molecule (functional monomers) by covalent and/or non-covalent bonding. In this stage, pre-organization of the binding sites is achieved by assembling the functional monomers around the template. (2) Polymerization in order to maintain the alignment of the functional group(s) which are optimally set for binding the template molecule. (3) Removal of the template from the resulting polymer matrices, allowing 'tailor-made' binding sites for the template molecule to be generated. A kind of snapshot of solution (or gas) is taken, and the structure of template is memorized in these polymers which provide the target receptors and they respond specifically to selective functional groups which enable them to be successful in sensors, chromatographic separations and catalysis.

For a long period of time, people have regarded solutions and gases as simple aggregates of randomly moving molecules. We can pick up molecule of any kind in the system and place these target molecules on desired sites in the snapshot. This method paves the way to the molecular devices (molecular memories, molecular machines, molecular computers, etc). No other methods have ever provided important receptors so easily, promptly, and economically. Tailor-made receptors thus obtained protect our earth from environmental disruption. The technique can be characterized by its simplicity as a synthetic strategy for designed binding sites, and the most significant advantage of the technique is that no detailed design of the binding sites is necessary before preparation, unlike the preparation of conventional artificial small molecule receptors.

Reference may be made to a publication by L. Charpentier et al, Analytica Chimica Acta, 1995, 318, 89-93 wherein a sensitive modified carbon paste electrode for the direct determination of cholesterol was reported. The biosensor was based on amperometric measurements. The electrode was modified with hydroxymethyl ferrocene and horseradish peroxidase. Cholesterol oxidase and cholesterol ester hydrolase were used in solution. The measured current was found to be linear with cholesterol concentration in the range $1 \times 10^{-6}$ to $1.5 \times 10^{-4}$ M. The measuring time was 30 seconds. The main problem was the biosensor was shown to be pH dependent and had to be stored at 4° C. for shelf life and the measurements were not carried out in real serum cholesterol samples.

Reference may be made to a publication by M. D. Marazuela et al, Biosensors & Bioelectronics, 1997, 12, 233-240 wherein free cholesterol fiberoptic biosensor for serum samples with simplex optimization was described. Silicone-entrapped tris(4,7-diphenyl-1,10-phenanthroline) ruthenium (II) complex, the luminescence of which was sensitive to oxygen changes, was used as an optical transducer of the oxidation of cholesterol by cholesterol oxidase. The biocatalyst was entrapped in a graphite powder layer deposited onto the dyed silicone film. The dynamic range of the biosensing membranes is found to be 0.15-3.0 mM of free cholesterol. The major problem was the interference due to the presence of ascorbic acid which gets oxidized by the dissolved oxygen in the samples rendering a false response.

Reference may be made to a publication by S. A. Piletsky et al, Sensors and Actuators 1999, B 60, 216-220 wherein molecular imprinting of cholesterol was achieved on gold surface by the simultaneous sorption of template and hexadecyl mercaptan molecules on the surface of gold electrode and the imprinted cavities have been used as channels for potassium ferricyanide which was reduced at the electrode surface. The change of potassium ferricyanide reduction peak has been related to the template concentration. The sensor gave a possibility of cholesterol detection in the 15-60 μM range. The analysis could be performed within 5 minutes. The main bottleneck was the loading of potassium ferricyanide in the imprinted cavities as the molecular recognition process running inside of these channels competes with the mass-transport of potassium ferricyanide to the electrode surface and consequently reduces the electrochemical signal which would subsequently lead to errors in measurement.

Reference may be made to a publication by Haiyan Wang and Shaolin Mu, Sensors and Actuators, 1999, B 56, 22-30 wherein cholesterol oxidase immobilized in polyaniline film was used to determine cholesterol amperometrically. The response current of the enzyme electrode increases linearly with increasing concentration of cholesterol in the range 0.05-0.5 mmol dm$^{-3}$ at 0.45 V and 0.05 to 0.2 mmol dm$^{-3}$ at 0.60 V for Triton X-100 of 5%, and 0.01 to 0.1 mmol dm$^{-3}$ at both potentials of 0.45 and 0.60 V for Triton X-100 of 1%. The major problem in this report was the drop in the response current of the enzyme to 51% of its initial value after 11 days.

Reference may be made to a publication by Manihar Situmorang et al, Talanta, 1999, 49, 639-649 wherein flow injection potentiometry (FIP) for the enzymatic determination of cholesterol was reported. The assay utilised a combination of three enzymes: cholesterol esterase (CE), cholesterol oxidase (COD) and peroxidase (POD). The method was developed by the use of a tungsten wire electrode as a sensor vs. Ag/AgCI in conjunction with a redoxmediator ferrocyanide. CE converts esterified cholesterol to free cholesterol, which is then oxidised by COD with hydrogen peroxide as product. Ferrocyanide is converted to ferricyanide by hydrogen peroxide, catalysed by POD, and the tungsten electrode responds to the ratio of ferricyanide to ferrocyanide. Flow injection potentiometry gave a fast response (30 s). Linear calibration was obtained from 0.05 to 3.0 mM cholesterol, with a slope of 60.2 mV/decade change in cholesterol concentration. The main drawback was the biosensor was sensitive to the presence of bacterium *E. coli* in blood serum because it consumes oxygen in solution and leads to a decrease in the enzymatic reaction. Also high concentrations of ascorbic acid and uric acid gave negative errors while that of lipids palmitic acid, tripalmitin and phosphatidyl colin gave positive errors in the calibration plots of standard cholesterol solutions.

Reference may be made to a publication by Manoj Ku. Ram et al, Biosensors and Bioelectronics, 2001, 16, 849-856 wherein enzyme multilayers such as PSS/PEI/COX, PSS/PEI/COX/PEI/CE, PSS/PEI/COX-CE/PEI were prepared on the surface of a platinum electrode, ITO coated glass plate, quartz crystal microbalance, quartz plates, mica and silicon substrates. Initially, a layer of polyanion, poly styrene sulfonate (PSS) was adsorbed followed by a layer of polycation, poly ethylene imine (PEI) on each solid substrate from aqueous solutions. The alternating layers were formed by consecutive adsorption of polycations(PEI) and negatively charged proteins (COX) and cholesterol esterase (CE). The amperometric measurements in the presence of cholesterol revealed saturation in current values at 1 mM concentration of cholesterol in solution. The stabilized response was obtained after 20-30 seconds. The major hurdle was the immobilization procedure for the enzyme which was tedious and involves numerous steps and results of the pains taking work were not impressive.

Reference may be made to a publication by C. Bongiovanni et al, Bioelectrochemistry, 2001, 54, 17-22 wherein an electrochemical amperometric biosensor for free cholesterol monitoring was described. The sensor was a bi-enzymatic electrochemical system in which horseradish peroxidase and cholesterol oxidase were simultaneously immobilized within a polymeric film, on the surface of a pyrolitic graphite electrode. The enzyme activity was determined using horseradish peroxidase coupled assay to quantify the rate of $H_2O_2$ formation. The response time was approximately 30 seconds. The main draw back of this protocol was that current peak height values show only a quasi-linear calibration, within the concentration range investigated i.e., from 0.04 to 0.27 mM. Also horseradish peroxidase may undergo inactivation in the presence of a high excess of the substrate. Membrane detachment from the electrode surface was sometimes observed after the first week from sensor fabrication.

Reference may be made to a publication by S. P. Martin et al, Analytica Chimica Acta, 2003, 487, 91-100 wherein an AT-cut quartz crystal sensor to measure in real-time the total cholesterol concentration in buffer and serum, using the trienzyme system of cholesterol esterase (ChE), cholesterol oxidase (ChOx) and horseradish peroxidase (HRP) was reported. The hydrogen peroxide produced from the ChE-ChOx reaction oxidises diaminobenzidine (DAB), in the presence of HRP. The response of the sensor to cholesterol was optimal in the presence of 0.1% (v/v) Triton X-100 at 0.2 U/ml ChOx, and 1 U/ml ChE. The response time was less than 25 minutes. For clinical measurement of total cholesterol using this method, a dilution (1/20) of the serum would be required. The major setback in this work was the concentration of high density lipoprotein (HDL) cholesterol could not be determined because it solubilised the oxidised DAB, leading to poor adsorption at the crystal surface. Also the response time was much higher than reported in other amperometric and potentitometric sensors wherein they report the response time in the order of seconds.

Reference may be made to a publication by Victoria Shumyantseva et al, Biosensors and Bioelectronics, 2004, 19, 971-976 wherein a screen-printed enzyme electrode based on flavocytochrome P450scc for amperometric determination of cholesterol was developed. They were disposable and the response time was 1-2 minutes. Enzyme immobilization was done on two types of substrates. A one-step method for RfP450scc immobilization in the presence of glutaraldehyde or by entrapment of enzyme within a hydrogel of agarose was presented. The sensitivity of the biosensor based on immobilization procedures of flavocytochrome P450scc by glutaric aldehyde was 13.8 nA $\mu M^{-1}$ and the detection limit was 300 $\mu M$ with a coefficient of linearity 0.98 for cholesterol in the presence of sodium cholate as detergent. The detection limits and the sensitivity of the agarose-based electrode were 155 $\mu M$ and 6.9 nA $\mu M^{-1}$ with a linearity coefficient of 0.99. The main drawback was that the biosensor was not tested in human serum for the detection of total cholesterol and interference due to ascorbic and uric acid in real samples remains to be examined.

Reference may be made to a publication by Juan-C. Vidal et al, Talanta, 2004, 64, 655-664 wherein three biosensor configurations like Pt/PB/PPy-ChOx, Pt/SAM/PB/PPy-ChOx Pt/SAM/PB/PPy-ChOx/Nf were tried as cholesterol amperometric sensors. The abbreviations were of: Pt, Platnium electrode as substrate; SAM, self assembled monolayers; PB, Prussian blue; PPy, polypyrrole, ChOx, Cholesterol oxidase; Nf, Nafion membrane. The enzyme was entrapped within a polypyrrole (PPy) layer electropolymerised on to the PB film. Of the three configurations, the one with Nafion was reported to be the best as it reduced the interference due to ascorbate and urate in the synthetic serum samples. The major inconvenience was the multiple steps involved in the immobilization of enzyme especially that of PB and PPy films thickness could not be controlled as they were deposited electrochemically. Such factors would subsequently lead to errors in the measurement of current.

Reference may be made to a publication by G. Li et al, Biosensors and Bioelectronics, 2005, 20, 2140-2144 wherein an amperometric biosensor for monitoring total cholesterol in blood is demonstrated with a combination of cholesterol esterase, cholesterol oxidase, peroxidase, potassium ferrocyanide and multi-walled carbon nanotubes immobilized on the screen-printed carbon electrodes. The modification of the carbon nanotubes promoted the electron transfer and offers a reliable calibration profile and stable electrochemical properties. The screen-printing method provides a way for rapid, economic and reproducible manufacture of sensor electrode. The main problem was the sensor was not instantaneous as its function was based on the production of hydrogen peroxide from cholesterol ester of the sample, which then gets reduced by potassium ferrocyanide and resulting current was noted to be proportional to the cholesterol content. Each measurement was made after 180 seconds of sample addition. With deviation from this time element, errors in detection can happen easily. However, this measuring system was affected by air oxidation of ferrocyanide that takes place as a competitive reaction during the enzymatic oxidation.

OBJECTIVES OF THE INVENTION

The main objective of the present invention is to provide a novel sensor for the quantitative estimation of total cholesterol in human blood serum using molecular imprint of cholesterol (MIPC) as sensing material.

Another objective of the present invention is to provide a novel sensor wherein ISFET (Ion Sensitive Field Effect Transistor) made of dual dielectric $SiO_2$—$Si_3N_4$ gate having a channel length L=12 microns and channel width W=4800 microns is used as a working electrode.

Yet another objective of the present invention is to provide a novel sensor wherein MIPC is deposited on the gate of the ISFET.

Yet another object of the present invention is to study the sensitivities of ISFET with and without MIPC layer on the gate towards cholesterol concentration range (150-250 mg/dl).

Still anther object is to study the ISFET response characteristics (a) without and (b) with MIPC layer on the gate by carrying out standardisation measurements in standard cholesterol solutions with concentrations in human blood serum range.

SUMMARY OF INVENTION

Accordingly the present invention provides a potentiometric sensor device for the quantitative estimation of total cholesterol in human blood serum and the said device comprising an ion exchange field effect transistor (ISFET), as a working electrode and Ag/AgCl, as a reference electrode, wherein the said ion exchange field effect transistor (ISFET) comprises P substrate (1), N+ source and drain regions (2,3), terminal connections for source and drains (4, 5), substrate connection (6), field oxide (7), and $SiO_2$+$Si_3N_4$ gate dielectric (8) and the said $SiO_2$+$Si_3N_4$ gate being coated with a layer of molecular imprint of cholesterol (MIPC).

In an embodiment of the present invention the molecular imprint of cholesterol (MIPC) used is an imprint prepared with a complex of cholesterol format (CCF) and 3-aminopropyltriethoxysilane (APTS) on a silica matrix.

In yet another embodiment the cholesterol sensor has the following characteristics:
 a) the sensor sensitivity to cholesterol is in the rage of 90-93 mV/decade;
 b) the respond of the sensor to cholesterol is in the range of 100-350 mg/dL;
 c) the response time is less than 1 minute; and
 d) the shelf life of the sensor is 90-95 days.

The present invention further provides a process for the preparation of potentiometric biosensor for the quantitative estimation of total cholesterol in human blood serum and the said process comprises the steps of:
 a) preparing an ion exchange field effect transistor (ISFET) having an open dielectric $SiO_2$—$Si_3N_4$ gate on p-type Czochralski silicon wafers by known method,
 b) reacting cholesterol chloroformate with 3-amminopropyl triethoxysilane in a weight ratio of 1.5:0.5 to 2.5:1.5 in dichloromethane, under stirring, in a ice bath, for a period of 5-10 hrs, followed by adding triethyl amine and further stirring for 10-14 hrs. to obtain the resultant product of the complex of cholesterol chloroformate (CCF) and 3-amminopropyl triethoxysilane (APTS),
 c) adding triethoxy silane drop wise to the above said resultant reaction product obtained in step (b) and subsequently adding ethanol and aqueous HCl having pH 2 in a ratio of 1.5:1 to 2.5:1.5 and stirring the reaction mixture for 5-7 days in an ice bath, followed by keeping it in an oil bath at a temperature of 40-45° C. for 22-26 h hrs and subsequently raising the temperature of the oil bath to 70-75° C. and heating the reaction mixture for 46-50 hrs, followed by the removal of product,
 d) washing the resultant product obtained in step (c) with acetone to remove the cholesterol template, followed by grounding to obtain the desired molecular imprinted monolith in powder form,
 e) preparing a slurry of the molecular imprinted monolith powder in acetone,
 f) applying the slurry of molecular imprinted monolith obtained in step (e) on the open dielectric $SiO_2$—$Si_3N_4$ gate of ion exchange field effect transistor (ISFET) of step (a), followed by the evaporation of acetone to obtain the desired working electrode cholesterol sensor.

In yet another embodiment the ion exchange field effect transistor prepared in step (a) comprises P substrate (1), N+ source and drain regions (2,3), terminal connections for source and drains (4, 5), substrate connection (6), field oxide (7), and $SiO_2$—$Si_3N_4$ dielectric gate (8).

In yet another embodiment the triethoxy silane used in step (c) is 2-4% of the product obtained in step (b).

In yet another embodiment the molecular imprinted monolith powder used in slurry obtained in step (e) is in the range of 200-500 mg per 0.4-1.0 mL of acetone.

In yet another embodiment the molecular imprinted monolith powder used in slurry obtained in step (e) is in the range of 200-500 mg per 0.5 mL of acetone.

Figure 2:
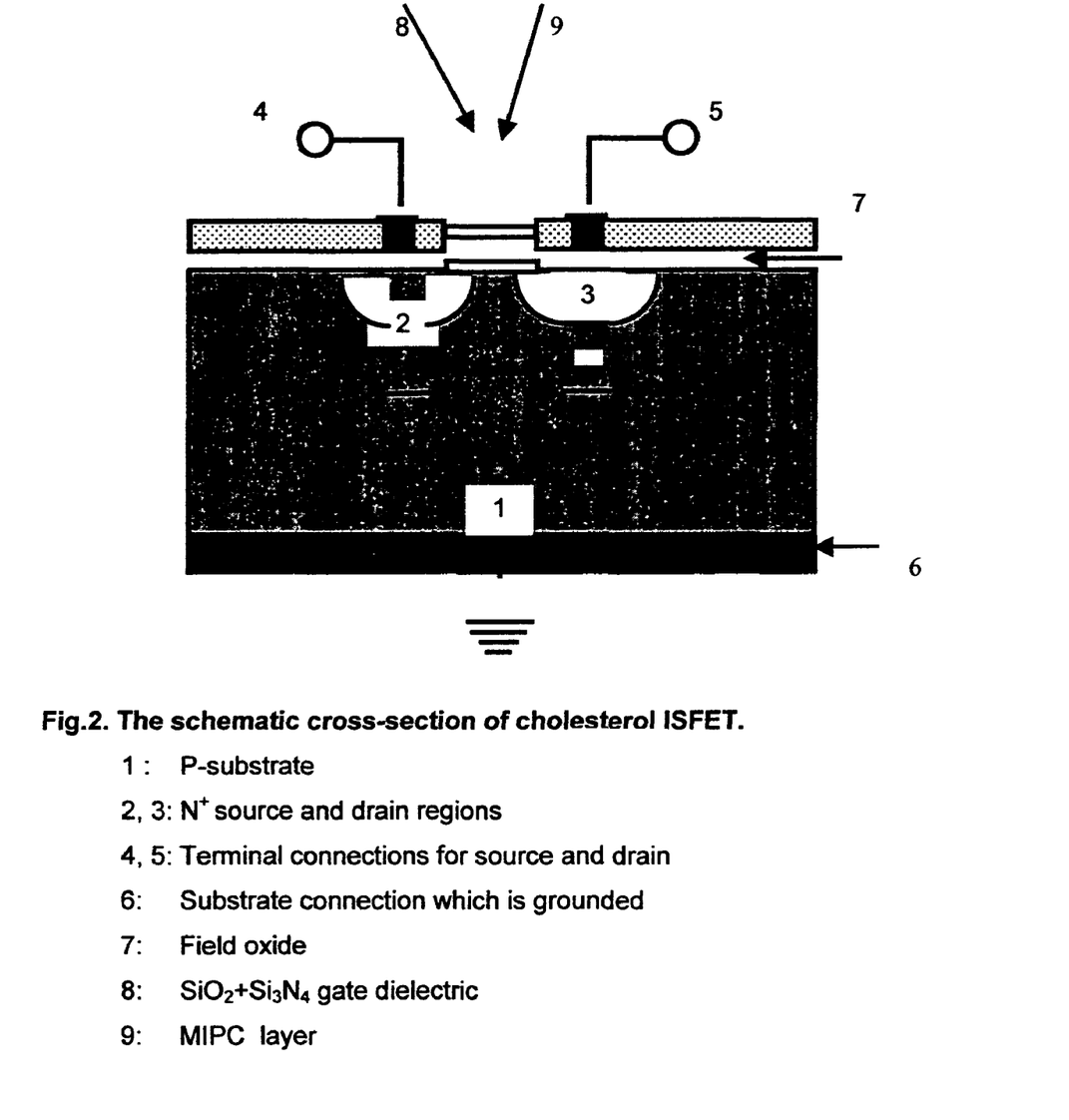
FIG. 2. Schematic cross-section of cholesterol ISFET.
Figure 3:
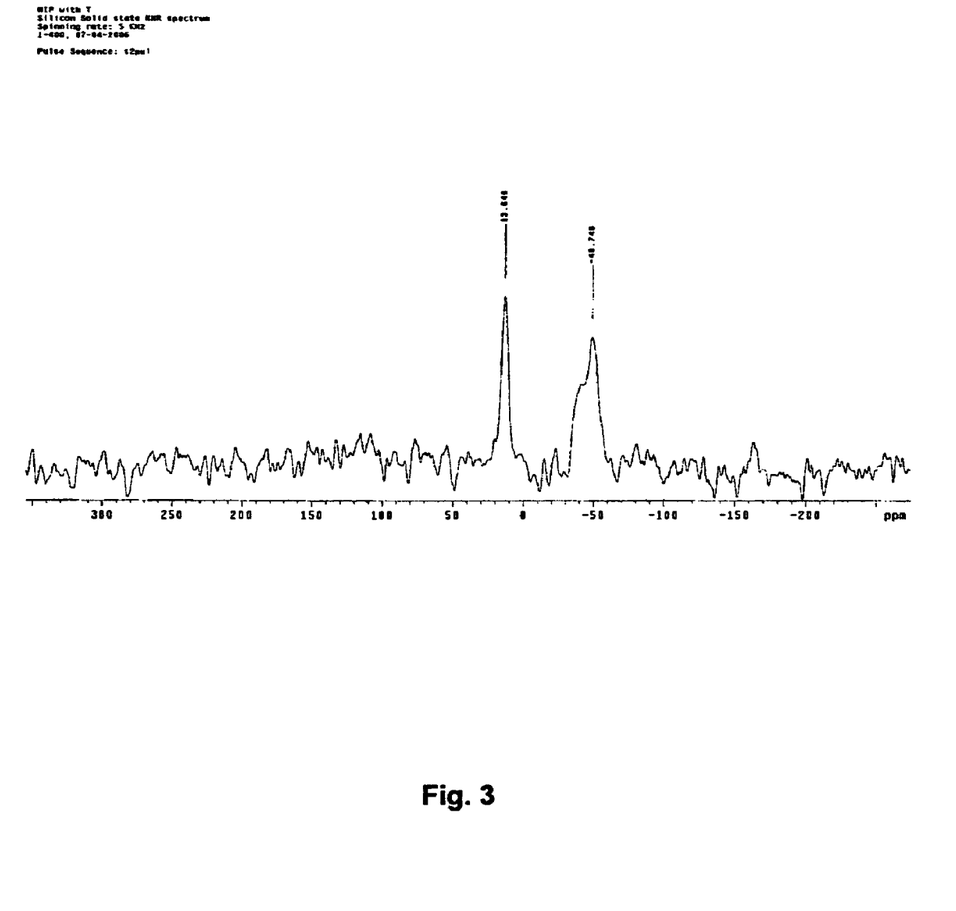
FIG. 3. Solid state $^{29}$Si NMR spectrum of silica polymer with the template cholesterol molecule anchored.
Figure 4:
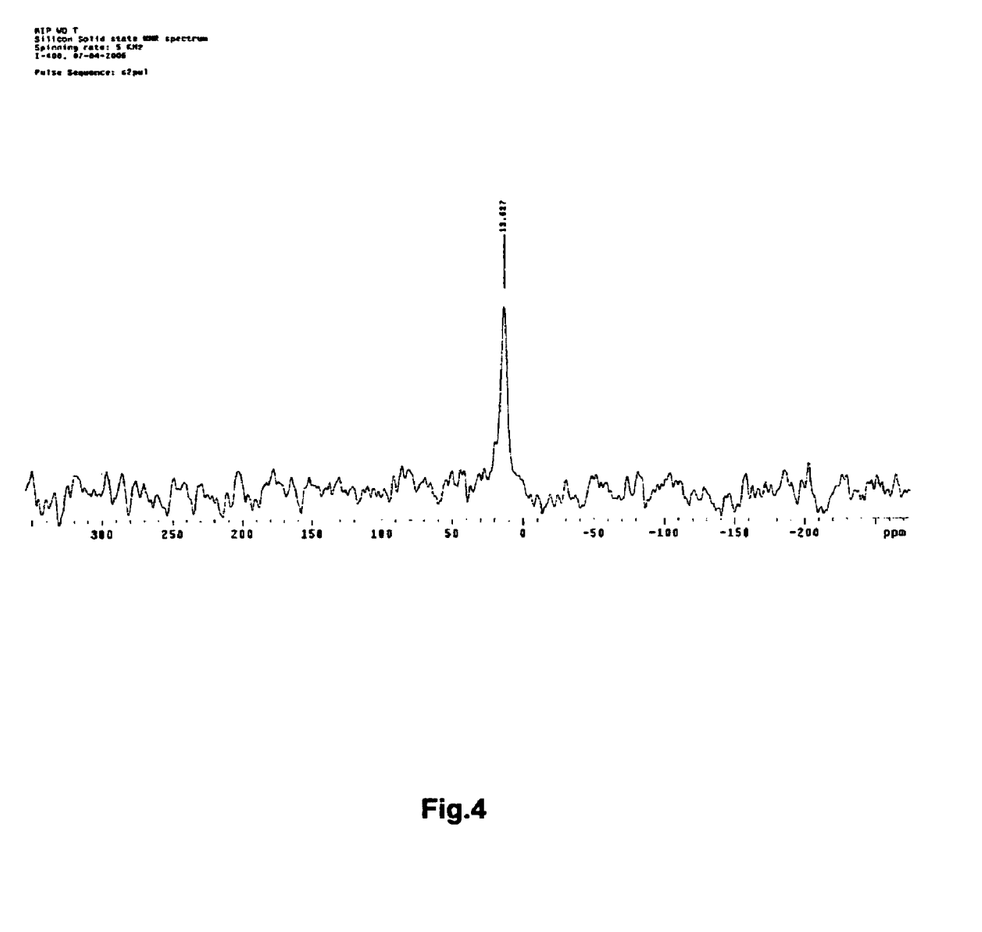
FIG. 4. Solid state $^{29}$Si NMR spectrum of material after cholesterol template removal (MIPC)

The present invention is the development of a biosensor to measure total cholesterol concentration in human blood serum. The biosensor operates on potentiometric mode and consists of molecular imprint of cholesterol (MIPC) as sensing material. ISFET (Ion-sensitive field effective transistor) with in-built Ag/AgCl reference electrode senses the concentration of cholesterol. FIG. 2 gives the details of ISFET. The originality of the present invention lies in identification of suitable sensing material as the molecular imprint of cholesterol anchored on a silica matrix. The uniqueness of the present invention provides a biosensor to determine total cholesterol in human blood serum without interference from other constituents in it. The innovation of the present invention to sense cholesterol potentiometrically without the help of added reagents to enhance the conductivity from the standard cholesterol solutions and human blood serum makes the strategy a milestone in the relevant scope of work. Addition of ferrocyanide or carbon nanotubes or carbon paste to increase the working efficiency of the biosensor did not arise; the use of enzymes like cholesterol esterase, cholesterol oxidase and horseradish peroxidase to sense cholesterol is replaced by a single entity of MIPC, thereby making the present invention superior and original to the already reported cholesterol biosensors. The performance of the biosensor is validated as it obeys Nernst law and gives a slope value of 92 mV/decade for the linear plot of potential vs. concentration. The departure from the ideal nernst behavior is due to the non-conductive nature of the cholesterol molecules which gets reflected on the imprint. This sub-nernstian behavior of MIPC coating is highly significant as against the slope value of 35.45 mV/decade obtained for the sole ISFET.

In one of the feature of the invention 200 mg of MIPC was made into a slurry using 0.5 ml of acetone and was applied on the surface of the gate. On exposure to air at room temperature, acetone evaporates at once and leaves behind the sensing material.

Figure 5:
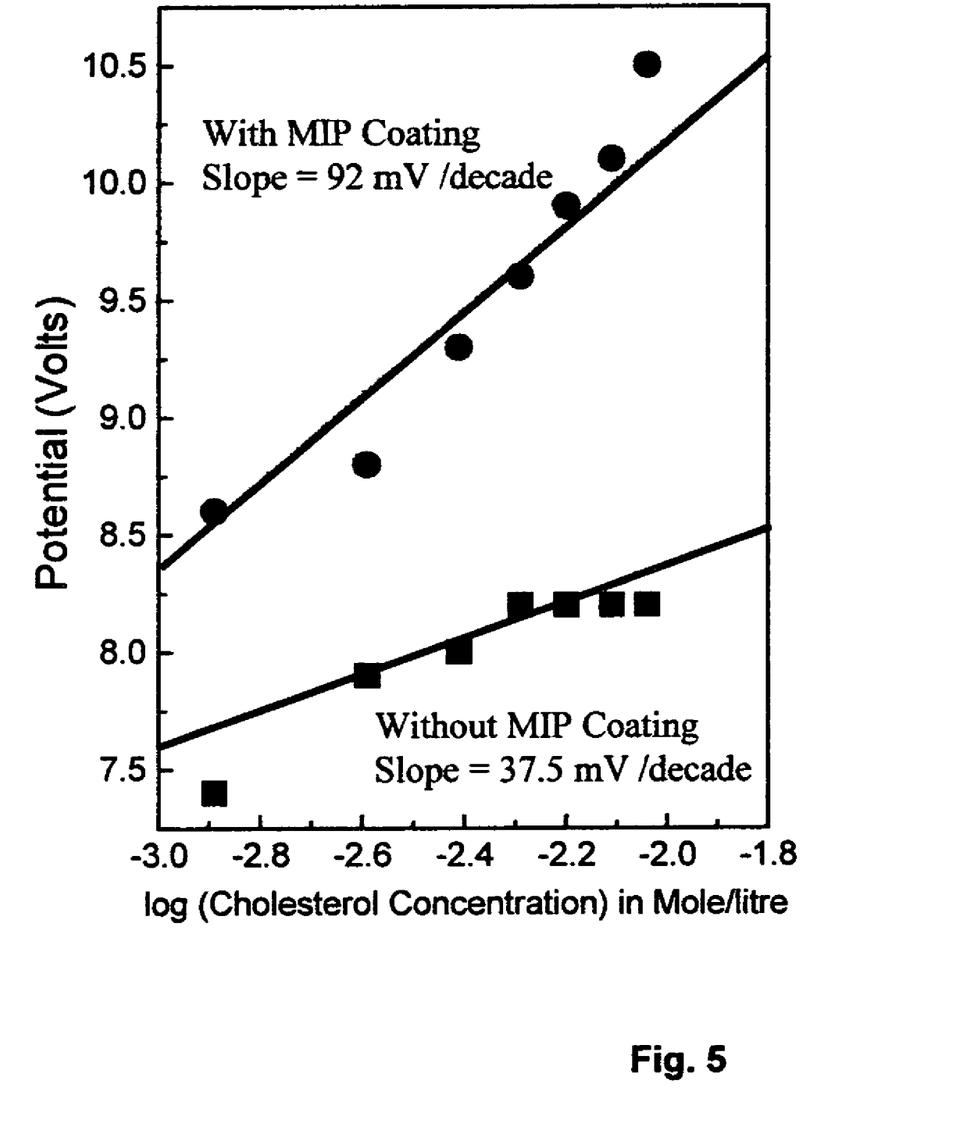
FIG. 5. Plot of potential Vs. Standard cholesterol concentration with and without MIPC coating on the ISFET gate.

In yet another feature of the invention, ISFET response characteristics (a) without and (b) with molecular imprint on the gate; standardization measurements have been carried out in the standard cholesterol solutions with concentrations in human blood serum range (FIG. 5).

Figure 6:
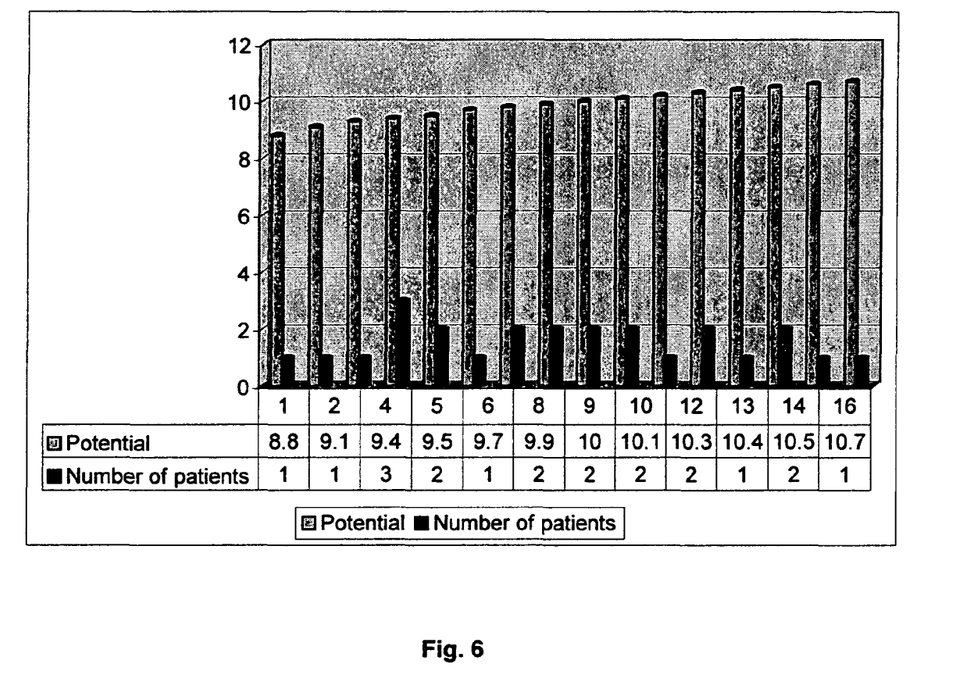
FIG. 6. Distribution of potential with number of patients.

In yet another feature of the invention, blood serum samples were tested for cholesterol concentration using ISFET-MIPC on gate and the output potential was recorded (FIG. 6).

Figure 7:
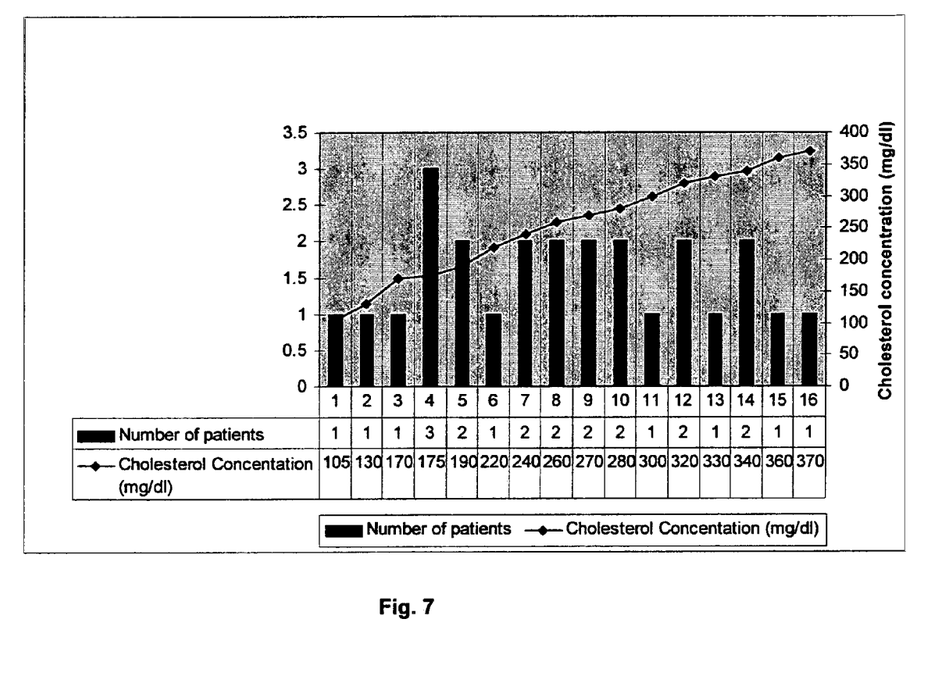
FIG. 7. Distribution of cholesterol concentration with number of patients.

In yet another feature of the invention the output potential corresponds to a specific value of cholesterol concentration. The distribution of cholesterol concentration in human blood serum agrees very well with the reported values (FIG. 7).

BRIEF DESCRIPTION OF THE DRAWINGS

Components 1 to 8 comprise the ISFET. Component 9, the MIPC layer coating on the gate, provides selectivity to the sensor for cholesterol. On trapping cholesterol molecules by the MIPC layer, the gate-source potential increases. The change in gate-source potential as a function of cholesterol concentration gives the calibration characteristic of the sensor.

DETAILED DESCRIPTION OF INVENTION

Accordingly, the present invention provides a novel and original biosensor to measure total cholesterol (150-250 mg/dl) in human blood serum using the potentiometric protocol. The working electrode is an ISFET, the gate of which is coated with a layer of molecular imprint of cholesterol and the reference is an inbuilt Ag/AgCl electrode. The imprinting of bulk amorphous silica with cholesterol functional groups is carried out by two major steps; first, the formation of a complex between the cholesterol template and a cross linking monomer like 3-amino propyl triethoxy silane; second, polymerization of the monomer using suitable reagents and the removal of the template molecules, to produce specific recognition sites on the imprinted polymer for the adsorption of the template. The triethoxy silane part of the moelcules' side groups is incorporated into the silica framework during sol-gel synthesis, and subsequent removal of the aromatic core creates a cavity with spatially organized aminopropyl groups covalently anchored to the pore walls. Triethylamine helps to bond the cholesterol template molecule to the triethoxy silane by the formation of a carbamate; the carbamate provides the linkage to the portion of the imprint that creates the void space (upon its removal) and provides spatial organization within the binding site (FIG. 1). Thus the molecular imprint of cholesterol (MIPC) on the silica could be highly specific in recognizing the receptor molecules in a solution with different organic functional groups and acts as an efficient and selective sensing material to determine cholesterol in human blood serum.

The uniqueness of the present invention lies in identifying a suitable sensing material as the molecular imprint of cholesterol anchored on a silica matrix, to determine total cholesterol in human blood serum without interference from other constituents in it. The innovation is to sense cholesterol potentiometrically without the help of added reagents to the sensing material to enhance the conductivity which makes the strategy a milestone in the relevant field. Addition of ferrocyanide or carbon nanotubes or carbon paste to increase the working efficiency of the biosensor did not arise; the use of enzymes like cholesterol esterase, cholesterol oxidase and horseradish peroxidase as sensing material to sense cholesterol is replaced by a single entity of MIPC, thereby making the present invention superior and original to the already reported cholesterol biosensors. The plot of potential vs. concentration of cholesterol for ISFET with MIPC gives a straight line with a positive slope value of 92 mV/decade indicating a sub-nemestian response as against the slope value of 35.45 mV/decade for the sole ISFET. The sub-nernstian response is expected due to the lack of conductivity of the cholesterol molecules that would have left behind a ghost of its property in the MIPC imprint. The response time of the MIPC sensor was less than a minute and the shelf life of the electrodes either in use or idle was found to be three months period. The electrode surface can be re-coated and used.

The following examples are given by the way of illustration and therefore, should not be construed to limit the scope of the invention.

EXAMPLE 1

Fabrication and Package of ISFET Device:

ISFET is fabricated of dual dielectric $SiO_2$—$Si_3N_4$ gate. The device has been fabricated on P-type Czochralski silicon wafers of resistivity 15-20 ohm-cm ($7.4 \times 10^{14}$ cm$^{-3}$) and orientation <100>. Fabrication technology of the ISFET, based on the NMOSFET technology comprised the following processing steps: (i) Field oxidation (1100° C., 30 min. dry $O_2$+120 min. wet $O_2$+30 min. dry $O_2$) giving oxide thickness=0.9 μm, (ii) First photolithography for source/drain N$^+$ diffusion and oxide etching, (iii) Phosphorous diffusion (1050° C., 30 min): Sheet resistance <3 ohms/square, (iv) Second photolithography for gate window, and oxide etching, (v) Gate oxidation (trichloroethylene ambient), 1000° C., 120 min., dry $O_2$, oxygen flow rate 2 liter/min, a little TCE vapour was carried down the tube by a slow bleed of $N_2$ through TCE bubbler at 25° C., $t_{ox}$=140 nm, (vi) Nitridation (LPCVD), 780° C., 25 min, initial pressure=0.02 torr, deposition pressure of dichlorosilane and ammonia gas mixture=0.2 ton, dichlorosilane=20 cc, ammonia 200 cc, gas ratio=1:10, $t_{Nitride}$=100 nm; annealed at 900° C. for 30 min in $N_2$, (vii) Third photolithography for contact holes, and oxide etching, (viii)

Sputtering of chromium (50 nm) and gold (500 nm), (ix) Fourth photolithography for metal pattern delineation, and metal etching, (x) Metal sintering, (xi) Wafer scribing, and chip sorting and mounting on ceramic substrate, (xii) Wire bonding, (xiii) Protecting the metal pads and wires by insulating epoxy (Epotek H 70E/H74, cured at 120° C., 30 min.) with soldering pads protected by RTV compound. The gate region has been left exposed.

EXAMPLE 2

Preparation of Molecular Imprint of Cholesterol (MIPC):

The schematic representation of the preparation of molecular imprint of cholesterol is given in FIG. 1. It involves the following 3 steps.

Step 1: To make Template Molecule

Cholesteryl Chloroformate (CCF) (0.449 gm) and 3-amino propyl triethoxy silane (APTS) (0.229 gm) were added to 20 ml of dichloromethane (DCM) in a 100 ml RB flask. The reaction mixture was kept in an ice bath and stirred for 5-10 minutes; then triethyl amine was added dropwise (1.25 ml) to the reaction mixture and stirring was continued for 12 hours.

Step 2: Adsorption of CCF on Silica Matrix

The weight of the resultant product (complex of CCF and APTS) of the first step was of 0.64 g. To this complex, 3% triethoxy silane (TEOS) with respect to the weight of the template weight and 70 ml of dry ethanol were added. Then subsequently, 34 ml of aqueous HCl (pH ~2.0) were added.

Step 3: Washing Imprint for the Surface Protection

The reaction mixture in the RB flask was covered with a loose cap, stirred for 6 days in the ice bath, then kept in an oil bath at 40° C. for 24 hours and later the temperature of the oil bath was increased to 70° C. and heated for 48 hours. Finally, the product was removed, washed with acetone and the imprinted monoliths were ground into powder.

EXAMPLE 3

Deposition of MIPC on the Gate Region of ISFET:

MIPC was made into a slurry using acetone and applied on the gate region of the ISFET and air dried.

EXAMPLE 4

Optimization of Coating on Gate:

200-500 mg of MIPC was mixed with 1 ml of acetone and coated on the surface of the ISFET gate. On drying acetone evaporates at once leaving a layer of MIPC on the ISFET gate.

EXAMPLE 5

Measurement Procedure:

Measurements have been carried out using an in-house assembled signal conditioning circuit for direct reading of pH. An Ag/AgCl reference electrode has been used. This circuit gives an output voltage equal to the pH of the solution in which the ISFET is immersed. The circuit including the ISFET has an overall voltage gain of 20. The measurements have been performed before and after crown ether layer deposition.

Concentration measurement involves the following steps.
a). Dipping the ISFET gate in the serum
b). Reading the potential
c). Matching the read potential with that of the standard values.

The Main Advantages of the Present Invention are as Follows:
1. The sensor can detect total cholesterol in human blood serum with high specificity even in 50 times diluted blood.
2. The sensing material identified is the molecular imprint of cholesterol (MIPC) anchored on to a silica matrix which has specific selectivity towards the cholesterol in presence of other organic constituents in human blood serum.
3. The chosen sensing material was the most convenient and very accessible to determine cholesterol in comparison to reported biosensors wherein the preparation of the relevant sensing material involves complicated steps, expensive solvents, two or more enzymes and externally added polymeric substrate.
4. The sensor was highly sensitive to cholesterol and specifically selective to it even to 50 times diluted samples of human blood serum.
5. The response time of the MIPC sensor was less than a minute.
6. The shelf life of the electrode either on use or idle was found to be a three months period.
7. The electrode surface can be re-coated and used.

We claim:

1. A potentiometric sensor device for the quantitative estimation of total cholesterol in human blood serum, the device comprising:
   an ion exchange field effect transistor; and
   a coating of a layer comprising a molecular imprint of cholesterol on a gate of the ion exchange field effect transistor;
   wherein the molecular imprint of cholesterol comprises an imprint prepared from a complex of cholesterol chloroformate and 3-aminopropyltriethoxysilane on a silica matrix.

2. A potentiometric sensor device for the quantitative estimation of total cholesterol in human blood serum, the device comprising:
   an ion exchange field effect transistor, as a working electrode; and Ag/AgCl, as a reference electrode;
   wherein the ion exchange field effect transistor comprises P substrate, N+ source and drain regions, terminal connections for source and drains, a substrate connection, field oxide, and $SiO_2+Si_3N_4$ gate dielectric, and the $SiO_2+Si_3N_4$ gate is coated with a layer comprising a molecular imprint of cholesterol; and
   wherein the molecular imprint of cholesterol comprises an imprint prepared from a complex of cholesterol chloroformate and 3-aminopropyltriethoxysilane on a silica matrix.

3. A sensor as claimed in claim 2:
   a) the sensor sensitivity to cholesterol is in the range of 90-93 mV/decade;
   b) the response of the sensor to cholesterol is in the range of 100-350 mg/dL;
   c) the response time of the sensor is less than 1 minute; and
   d) the shelf life of the sensor is 90-95 days.

4. A sensor as claimed in claim 2, wherein the shelf life of the sensor is 90-95 days.

5. A sensor as claimed in claim 2, wherein
   the response of the sensor to cholesterol is in the range of 100-350 mg/dL.

6. A sensor as claimed in claim 2, wherein the sensor sensitivity to cholesterol is in he range of 90-93 mV/decade.

7. A sensor as claimed in claim 2, wherein the shelf life of the sensor is at least 90 days.

8. A sensor as in claim 2, wherein
   the response time of the sensor is less than 1 minute.

9. A process for the preparation of a potentiometric biosensor for the quantitative estimation of total cholesterol in human blood serum, the sensor having an ion exchange field effect transistor as a working electrode and Ag/AgCl, as a reference electrode, wherein said ion exchange field effect transistor comprises P substrate, N+ source and drain regions, terminal connections for source and drains, a substrate connection, field oxide, and $SiO_2+Si_3N_4$ gate dielectric and the $SiO_2+Si_3N_4$ gate is coated with a layer comprising a molecular imprint of cholesterol, the process comprising:

a) preparing an ion exchange field effect transistor having an open $SiO_2$-$Si3N_4$ gate dielectric on a p-type substrate;

b) reacting cholesterol chloroformate with 3-aminopropyltriethoxysilane in a weight ratio of 1.5:0.5 to 2.5:1.5 in dichloromethane, under stirring, in an ice bath, for a period of 5-10 hrs, followed by adding triethylamine and further stirring for 10-14 h to obtain a complex of cholesterol chloroformate and 3-aminopropyltriethoxysilane;

c) adding triethoxysilane drop-wise to the reaction product obtained in step (b) and subsequently adding ethanol and aqueous HCl having pH 2 in a ratio of 1.5:1 to 2.5:1.5 and stirring the reaction mixture for 5-7 days in an ice bath, followed by keeping the reaction mixture in an oil bath at a temperature of 40-45° C. for 22-26 h and subsequently raising the temperature of the oil bath to 70-75° C. and heating the reaction mixture for 46-50 h, followed by the removal of product, d) washing the product obtained in step (c) with acetone to remove the cholesterol template, followed by grinding to obtain the molecular imprinted monolith in powder form, e) preparing a slurry of the molecular imprinted monolith powder in acetone, f) applying the slurry of molecular imprinted monolith obtained in step (e) on the open dielectric $SiO_2$—$Si_3N_4$ gate of the ion exchange field effect transistor prepared in step (a), followed by the evaporation of acetone to obtain the desired working electrode cholesterol sensor.

10. A process as claimed in claim 9, wherein the triethoxysilane used in step (c) is 2-4% of the product obtained in step (b).

11. A process as claimed in claim 9, wherein the sensor obtained has the following characteristic:
the sensor sensitivity to cholesterol is in the rage of 90-93 mV/decade.

12. A process as claimed in claim 9, wherein the proportion of molecular imprinted monolith powder used in the slurry obtained in step (e) is in the range of 200-500 mg per 0.4-1.0 mL of acetone.

13. A process as claimed in claim 12, wherein the proportion of molecular imprinted monolith powder used in the slurry obtained in step (e) is in the range of 200-500 mg per 0.5 mL of acetone.

* * * * *